United States Patent [19]

Bonte et al.

[11] Patent Number: 5,607,693
[45] Date of Patent: Mar. 4, 1997

[54] COSMETIC OR PHARMACEUTICAL COMPOSITION, ESPECIALLY DERMATOLOGICAL COMPOSITION, CONTAINING OXYACANTHINE, INTENDED IN PARTICULAR FOR STIMULATING HAIR GROWTH OR RETARDING HAIR LOSS

[75] Inventors: Frédéric Bonte; Alain Meybeck, both of Courbevoie, France

[73] Assignee: LVMH Recherche, Colombex Cedex, France

[21] Appl. No.: 457,303

[22] Filed: Jun. 1, 1995

Related U.S. Application Data

[63] Continuation of Ser. No. 119,051, filed as PCT/FR92/00235, Mar. 13, 1992, abandoned.

[30] Foreign Application Priority Data

Mar. 14, 1991 [FR] France ................. 91 03120

[51] Int. Cl.⁶ .................................. A61K 9/127
[52] U.S. Cl. ................. 424/450; 514/308; 514/880; 424/195.1
[58] Field of Search ............... 424/450, 195.1; 514/308, 880

[56] References Cited

U.S. PATENT DOCUMENTS

| | | | |
|---|---|---|---|
| 4,057,620 | 11/1977 | Prugnaud | 424/35 |
| 4,104,373 | 8/1978 | Sichert | 424/195 |
| 5,165,935 | 11/1992 | Andre | 424/450 |

FOREIGN PATENT DOCUMENTS

| | | |
|---|---|---|
| 0087993 | 9/1983 | European Pat. Off. |
| 0107559 | 5/1984 | European Pat. Off. |
| 2510402 | 2/1983 | France |
| 2609390 | 7/1988 | France |
| 2050166 | 1/1981 | United Kingdom |
| 2136812 | 9/1984 | United Kingdom |

OTHER PUBLICATIONS

Gregoriads in TIPS, Jul. 1983, p. 304.
Mezi. Life Sciences 26, 1473, 1980.
Patent Abstracts of Japan; vol. 14; No. 211 (C–715) (4154) 2 May 1990 & JP, A, 2 048 517 (Shiseido Co. Ltd.) 19 Feb. 1990.
Patent Abstracts of Japan; vol. 8, No. 199 (C–242) (1636) 12 Sep. 1984 & JP, A, 59 088 411 (Raion K.K.) 22 May 1984.
Patent Abstract of Japan; vol. 10, No. 71 (C–334) (2128) 20 Mar. 1986 & JP, A, 60 209 508 (Kaken Shiyouyaku K.K.) 22 Oct. 1985.

Primary Examiner—Gollamudi S. Kishore
Attorney, Agent, or Firm—Beveridge, DeGrandi, Weilacher & Young LLP

[57] ABSTRACT

The invention relates to a cosmetic or pharmaceutical composition which comprises oxyacanthine, one of its derivatives, one of their cosmetically or pharmaceutically acceptable acid addition salts or an extract of a plant in which it is present, such as Berberis vulgaris or barberry. One particular association is that of oxyacanthine with a saponin. This composition can be intended in particular for stimulating hair growth, retarding hair loss or combating pruritus.

52 Claims, 7 Drawing Sheets

FIG.4

COSMETIC OR PHARMACEUTICAL COMPOSITION, ESPECIALLY DERMATOLOGICAL COMPOSITION, CONTAINING OXYACANTHINE, INTENDED IN PARTICULAR FOR STIMULATING HAIR GROWTH OR RETARDING HAIR LOSS

This application is a continuation of application Ser. No. 08/119,051, filed as PCT/FR92/00235 Mar. 13, 1992, now abn., which application is entirely incorporated herein by reference.

The present invention relates essentially to a cosmetic or pharmaceutical composition, especially dermatological composition, containing oxyacanthine, intended in particular for stimulating hair growth or retarding hair loss. The oxyacanthine can be used as such or in the form of derivatives, in particular an acylated derivative such as the acetyl or propionyl derivative, or an alkylated derivative such as the methyl derivative, or its salts, especially its acid addition salts. In particular, the derivatives in question involve the phenolic hydroxy group of the oxyacanthine, which is generally numbered in the 12'-position of the oxyacanthane skeleton according to the nomenclature used in Chemical Abstracts. The oxyacanthine can be used on its own or in combination with at least one saponin. The oxyacanthine can be extracted from a plant selected especially from the following species: Berberis, Mahonia, Laurelia, Cocculus and Xanthorhiza, or can take the form of an extract of this plant.

In particular, the plants of the genus Berberis are well known, especially because they are commonplace and because of the fact that they grow over the greater part of Europe, notably in England, in North Africa and in the temperate zones of Asia. It is also used as an ornamental plant in gardens. The plants of the genus Berberis are known to contain a large number of active substances and principally berberine. Of the other substances, oxyacanthine is known.

Oxyacanthine has already been described in the document Chem. Pharm. Bull. (1976) vol. 24, no. 10, pages 2413–20, as having an antitumoral effect and in the document RO-63427 as being an active agent in hepatobiliary diseases.

According to the present invention, it has been discovered, surprisingly, that oxyacanthine, or its derivatives or salts, is effective in prolonging the active growth phase of the hair (anagenic phase) and, consequently, is capable of slowing down hair loss. It has further been discovered that oxyacanthine, or its derivatives or salts, is active on pruritus, especially pruritus of the scalp, which frequently accompanies hair complaints.

Thus one object of the present invention is to solve the novel technical problem consisting in the provision of a novel formulation of a cosmetic or pharmaceutical composition, especially dermatological composition, which is effective on hair growth, the slowing-down of hair loss and pruritus.

A further object of the present invention is to solve this novel technical problem by proposing a novel formulation of enhanced efficacy through the use of the effects of combining active substances.

The present invention makes it possible to solve these novel technical problems for the first time in a manner which is satisfactory, reliable and inexpensive and which can therefore be used on the industrial scale.

Thus, according to a first feature, the present invention provides a cosmetic composition, intended in particular for stimulating hair growth, retarding hair loss or combating pruritus, especially pruritus of the scalp, which comprises, as active ingredient, a cosmetically effective amount of oxyacanthine or one of its derivatives or salts, in particular the derivatives involving the phenolic hydroxy group of the oxyacanthine, preferably of formula (I) below:

in which:

R is a hydrogen atom (oxyacanthine), a $C_2$–$C_{12}$-acyl radical or a $C_1$–$C_{12}$ hydrocarbon chain, or one of its acid addition salts, in particular one which is cosmetically acceptable, or a plant extract containing oxyacanthine or one of its derivatives as defined above.

It will be noted that oxyacanthine derivatives generally have the advantage of being more stable than oxyacanthine itself.

In one particular variant, the hydrocarbon chain and the acyl radical can be saturated or unsaturated and linear, branched or partly cyclic, especially aromatic.

In one advantageous variant, R is in particular a methyl, hexyl, decyl, acetyl, propionyl, butanoyl, hexanoyl or octanoyl radical, preferably a methyl, acetyl or propionyl radical.

A synthesis of the alkylated derivatives has been described especially in the document JP-02-111 777 relating to anticancer agents.

The methylated derivative (R=methyl) can either by synthesized by the method described below or the method described by P. DUTE et al. in Phytochemistry 1988, volume 27, no. 2, pages 655–657, or else it can be extracted from a plant, especially from Berberis cretica, Berberis pseudambalata, B. stolonifera, Berberis laurina, Laurelia sempervirens or Mahonia repens.

The acylated derivatives, such as the acetate and propionate in particular, can be prepared by a conventional method of acylation such as that described by P. DUTE et al. in Phytochemistry 1988, volume 27, no. 2, pages 655–657, or in the document JP-03-68 578.

Specifically, to acetylate the phenolic hydroxy group of oxyacanthine, the oxyacanthine is dissolved in dichloromethane, and 10 equivalents of acetic anhydride and 1 equivalent of pyridine are added, p-dimethylaminopyridine also being present as a catalyst. After dilution in dichloromethane, the pyridines are removed by washing with an alkaline aqueous solution and the excess acetic anhydride is then removed by washing with an aqueous acid solution. The organic phase is concentrated and the hydrochloride of the oxyacanthine acetate is then prepared in conventional manner, said hydrochloride precipitating.

In one particular embodiment, the composition as defined above contains oxyacanthine sulfate or a mixture of sulfates of tertiary bases including oxyacanthine sulfate, this mixture generally being prepared from a plant extract.

In another particular embodiment of the invention, the above-mentioned plant extract is an extract of a plant selected from the following species: Berberis, in particular: *B. amurensis* Rupr., *B. boliviana* Lechl., *B. bumeliaefolia* Schneid., *B. buxifolia, B. chingii* Cheng., *B. coriaria, B. cretica, B. dielsiana* Fedde., *B. integerrima, B. julianea* Schneid., *B. koreana* Palib., *B. laurina, B. nummularia, B. oblonga, B. orthobotrys, B. paucidentata* Rusby, *B. polyantha* Hemsl., *B. poiretii* Schneid., *B. pseudambalata, B. sargentiana* Schneid., *B. silva-taroucana* Schneid., *B. soulieana* Schneid., *B. stolonifera, B. vernae* Schneid., *B. vulgaris*, or barberry, and *B. wilsonae* Hemsl.; Mahonia, in particular: *M. repens* and *M. aquifolia*; Laurelia, in particular: *L. sempervirens*; Cocculus, in particular: *C. laurifolius*; and Xanthorhiza, in particular: *X. simplicissima*.

The parts of the plant used for the preparation of said extract are the leaves, the stems, the roots and the berries and preferably the bark of the stems or roots.

In one preferred variant, the above-mentioned extract is an extract of Berberis with the exclusion of Berberis thunbergii, preferably being selected from Berberis vulgaris, *B. cretica, B. pseudambalata, B. stolonifera* and *B. laurina*, in particular an extract of the root bark of this plant.

In one advantageous embodiment, the concentration by weight of oxyacanthine, one of its derivatives, one of its acid addition salts or a plant extract in which it is present, as mentioned above, is between 0.001% and 5%, preferably between 0.01% and 2%, based on the total weight of the composition.

According to a second feature, the present invention provides a cosmetic or pharmaceutical composition, especially dermatological composition, intended in particular for stimulating hair growth, retarding hair loss or combating pruritus, especially pruritus of the scalp, which comprises, as active ingredient, a cosmetically or pharmaceutically effective amount of an association consisting of oxyacanthine, its derivatives or its salts, preferably of formula (I) given above, one of its acid addition salts, in particular one which is cosmetically or pharmaceutically acceptable, or a plant extract in which it is present, with at least one saponin.

In one particular embodiment, the above-mentioned acid addition salt and plant extract are as defined previously.

In one advantageous embodiment of the invention, the above-mentioned saponin is selected from the group comprising the steroid saponins, especially the saponins containing sapogenin of the "diosgenin" type and those containing sapogenin of the "sarsapogenin" type, and the triterpene saponins, especially the saponins containing sapogenin of the "oleanane" structure, such as oleanolic acid, medicagenic acid, sapogenol or hederagenin, and those containing sapogenin of the "ursane" structure, such as ursolic acid or asiatic acid.

In one preferred variant, the saponin used to carry out the present invention is extracted from one of the following plants: Tribulus terrestris, Dioscorea, Smilax excelsa, Paris polyphylla, Cornus florida, Yucca, Smilax aristolochiaefolia, Asparagus officinalis, Hedera helix, Medicago—in particular *Medicago sativa* or lucerne—Centella asiatica and Trigonella fenugraecum.

In one advantageous variant, the above-mentioned composition contains a mixture of saponins extracted from one of the above-mentioned plants, in particular from *Medicago sativa*.

In one advantageous embodiment, the concentration by weight of oxyacanthine, its derivatives or one of its acid addition salts, as mentioned above, is between 0.001% and 5%, preferably between 0.01% and 2%, based on the total weight of the composition.

In one advantageous embodiment of the invention, the relative proportions of oxyacanthine, one of its acid addition salts or a plant extract in which it is present, and of a saponin or a mixture of saponins, as mentioned above, can vary within wide limits. Ratios of 10/1 to 1/10 by weight are preferred, this ratio preferably being 1/1 by weight.

The present invention can be carried out using commercially available oxyacanthine, in particular in the form of an acid addition salt such as the sulfate, which is available for example from EXTRASYNTHESE Genay-France.

The oxyacanthine derivatives of formula (I) given above can be prepared in conventional manner by synthesis procedures well known to those skilled in the art, the main procedures having been stated above. Those skilled in the art may also refer to the synthesis example given below.

The oxyacanthine, its derivatives or an addition salt can also be obtained from a plant, such as a plant of one of the above-mentioned species, in particular the species Berberis. Certain preparative methods have been described for example by A. ORECHOW in Archiv der Pharmazie (1933) 271, 323–27, or by P. PETCU and T. GOINA in Planta Medica (1970) 18 (4), 372–5.

In particular, the following method can be used to obtain a mixture of tertiary bases, including oxyacanthine, from a plant such as defined above. The previously ground plant material is moistened with 25% aqueous ammonia. The whole is macerated in the presence of ethyl acetate, at a rate of approximately 35 parts of solvent to one part of plant material, for 24 h. The mixture is then leached with ethyl acetate, after which the organic phase is extracted with a 2% dilute aqueous solution of sulfuric acid. The aqueous phase obtained is then rendered alkaline with aqueous ammonia in the presence of chloroform. After decantation, the aqueous phase is then re-extracted with chloroform. The chloroform phases are combined and then washed with water and dried. The chloroform is subsequently evaporated off to give a mixture of tertiary bases including oxyacanthine.

This mixture can be used to prepare an acid addition salt of these bases, especially a sulfate, by the following procedure.

The mixture of bases obtained by the method described above is introduced into a sufficient amount of acetone to dissolve it. The solution is acidified to pH 3 with concentrated sulfuric acid, which causes the bases to precipitate in the form of sulfates. After filtration, the crystals are dissolved in methanol. The methanol solution is then evaporated to dryness to give a mixture of water-soluble sulfates of tertiary bases, including oxyacanthine sulfate.

In yet another particular embodiment of the invention, the above-mentioned plant extract containing oxyacanthine is obtained by the following extraction method. The dry matter, preferably consisting of the root cortex of the plant defined above, is extracted by means of a solvent selected from the group consisting of alcohols preferably containing from 1 to 4 carbon atoms and organic esters preferably containing from 3 to 6 carbon atoms, or by means of a mixed solvent based on any mixture of the above-mentioned solvents, or an aqueous-alcoholic mixture.

Advantageously, the primary extraction solvent is methanol, ethanol, ethyl acetate, a methanol/water mixture or an ethanol/water mixture.

The ratio of the plant material to the extraction agent is generally between 1:5 and 1:20 parts by weight, but is preferably about 1:10 parts by weight.

Furthermore, it can be advantageous to render the dry matter alkaline, for example with aqueous ammonia, before performing the primary extraction.

The primary extraction is carried out at temperatures between room temperature and the boiling point of the solvent used for the extraction.

Preferably, the primary extraction is carried out under reflux, under atmospheric pressure, for a period of 2 to 4 h. Moreover, it is advantageously preceded by maceration in the cold extraction solvent for 2 to 4 h.

When the extraction is complete, the solvent phase containing the extract is filtered and then concentrated and/or evaporated to dryness under reduced pressure to give a first oxyacanthine-containing extract according to the invention.

In the case where the primary solvent contains water, for example an aqueous-alcoholic mixture containing 30% by weight of alcohol, it is preferable to remove the solvent, after filtration, by lyophilization at −80° C.

Furthermore, when the oxyacanthine, its derivatives, one of its acid addition salts or a plant extract in which it is present is associated, according to the present invention, with at least one saponin, the latter can also be obtained by extraction from plants, in particular from those mentioned above. Methods of extracting saponins are known, in particular from the following documents: U.S. Pat. Nos. 3,351,582, 3,449,760, 3,620,919, DE-2 118 916, SU-403 409, GB-1 378 278 and U.S. Pat. No. 3,901,875, or else from the publication by G. Massiot et al. in J. Agric. Food Chem. (1988) 36 (5), 902–909.

More particularly, as regards the extraction of saponins from Medicago, in particular from *Medicago sativa*, it will be preferable to use the method described by G. Massiot et al. in the document cited above, or the method described in French patent application FR 90-14542.

In one variant, the cosmetic or pharmaceutical composition, especially dermatological composition, according to the invention also comprises an effective concentration of at least one other active substance selected from quinine or its derivatives, rubefacients such as methyl nicotinate, a papilla fibroblast culture supernatant such as that defined in the document EP-A-272 920, keratin hydrolyzates, trace elements such as zinc, selenium and copper, 5-α-reductase inhibitors such as progesterone, cyproterone acetate, minoxidil, azelaic acid and its derivatives, or a 4-methyl-4-azasteroid, in particular 17-β-N,N-diethylcarbamoyl-4-methyl-4-aza-5-α-androstan-3-one, or else an extract of Serenoa repens.

According to a third feature, the present invention also covers the use, as an active ingredient, of oxyacanthine, one of its derivatives, preferably of formula (I) given above, one of its acid addition salts, in particular those which are cosmetically or pharmaceutically acceptable, or a plant extract in which it is present, by itself or in association with at least one saponin, for the manufacture of a cosmetic or pharmaceutical composition, especially dermatological composition, intended for stimulating hair growth, retarding hair loss or combating pruritus, especially pruritus of the scalp.

In one particular embodiment, the above-mentioned addition salt, plant extract and saponin, as well as the concentrations by weight of the active ingredients and their relative proportions, are as defined previously.

The cosmetic or pharmaceutical compositions, especially dermatological compositions, according to the present invention can be applied topically for the activity stated above, in particular in compositions presented in the form of a cream, gel or lotion and intended for application to the scalp.

According to a fourth feature, the present invention also provides a method of treatment intended for promoting hair growth, retarding hair loss or combating pruritus, especially pruritus of the scalp, which comprises applying, to the area to be treated, an amount, effective for achieving said desired effect, of oxyacanthine, one of its derivatives, preferably of formula (I) given above, one of its acid addition salts or a plant extract in which it is present.

In one particular embodiment, the above-mentioned oxyacanthine salt and plant extract are as defined previously.

In another advantageous embodiment, the above oxyacanthine, one of its acid addition salts or the plant extract in which it is present is associated with at least one saponin as defined previously.

According to a fifth feature, the invention also provides a method of manufacturing a cosmetic or pharmaceutical composition, especially dermatological composition, intended in particular for stimulating hair growth, retarding hair loss or combating pruritus, especially pruritus of the scalp, which comprises using oxyacanthine, one of its derivatives, preferably of formula (I), one of its acid addition salts, in particular a cosmetically or pharmaceutically acceptable acid addition salt, or a plant extract in which it is present, which is mixed with a pharmaceutically or cosmetically acceptable excipient, vehicle or carrier. In one variant, the oxyacanthine, its derivatives or one of its acid addition salts, as mentioned above, or the plant extract in which it is present, is associated with at least one saponin.

According to any one of the preceding features of the invention, the active substance of the invention, namely the oxyacanthine, its derivatives or salts or a plant extract in which it is present, can be used in the presence of hydrated lipidic lamellar phase or of liposomes, which may or may not incorporate said active substance. It is specified that the expression "incorporating" covers the case where the substance is totally incorporated and the case where only a certain amount of this substance is incorporated into the hydrated lipidic lamellar phases or the liposomes.

The term "lipidic" employed in the present document covers all substances which comprise a so-called fatty hydrocarbon chain generally containing more than 5 carbon atoms, this substance usually being called a "lipid".

According to the invention, the lipids used to form either the lipidic lamellar phases or the liposome-type vesicles are amphiphilic lipids, i.e. lipids consisting of molecules which possess either an ionic or a non-ionic hydrophilic group and a lipophilic group, these amphiphilic lipids being capable of forming lipidic lamellar phases or liposome-type vesicles in the presence of an aqueous phase, depending on the amount of water in the mixture.

The following may be mentioned in particular among these lipids: phospholipids, phosphoaminolipids, glycolipids, polyoxyethylenated fatty alcohols and optionally polyoxyethylenated polyol esters. Such substances consist for example of an optionally hydrogenated egg or soya lecithin, a phosphatidylcholine, a phosphatidylserine, a sphyngomyelin, a cerebroside or an oxyethylenated polyglycerol stearate.

It is preferable according to the invention to use a mixture of lipids consisting of at least one amphiphilic lipid and at least one hydrophobic lipid such as a sterol like cholesterol or β-sitosterol. The amount of hydrophobic lipid, expressed in mol, must not generally exceed the amount of amphiphilic lipid and preferably must not exceed 0.5 times this amount.

The above-mentioned active substance used according to the present invention can be incorporated into hydrated lipidic lamellar phases or into liposomes by known preparative techniques described for example in the document U.S. Pat. No. 4,508,703, if appropriate in combination with the document U.S. Pat. No. 4,621,023.

As is evident from the known properties of liposomes, depending on whether the substance to be incorporated is of lipophilic or hydrophilic character, it is incorporated either at least partially into the bilayers of the lipidic phase of the hydrated lipidic lamellar phases or the liposomes, or, respectively, into the aqueous phase. Thus the oxyacanthine is incorporated into said lipidic phase.

According to any one of the preceding features of the invention, the preferred minimum concentration of oxyacanthine, its derivatives or its salts in the plant extract is about 0.001%.

Also, according to any one of the preceding features of the invention, one advantageous embodiment relates to the association oxyacanthine, its derivatives or salts or an extract in which it is present, such as the extract of *B. vulgaris*, with minoxidil; preferably, the oxyacanthine, its derivatives or salts or the extracts in which it is present being incorporated into the hydrated lipidic lamellar phase or the liposome, the whole being mixed with an excipient compatible with these active. products, or else the association is produced from the separately packaged products, either in the form of a mixture prepared immediately before use, or by substantially simultaneous or successive applications of these products to the areas to be treated.

Other objects, characteristics and advantages of the invention will become clearly apparent from the following explanatory description referring to several Examples, which are given solely by way of illustration and consequently cannot in any way limit the scope of the invention.

The percentages are expressed by weight in the Examples, unless indicated otherwise. In the case of the extracts, the percentages are expressed by dry weight of the extract.

EXAMPLE 1

Preparation of a mixture of sulfates of tertiary bases from root barks of *Berberis vulgaris* or barberry 500 g of dried root barks of *Berberis vulgaris* are ground and moistened with about 300 ml of 7N aqueous ammonia. 18 l of ethyl acetate are poured on to the whole and the mixture is macerated for 24 h. It is filtered to recover on the one hand the filtrate and on the other hand the residue, which is leached with about 30 l of ethyl acetate. The filtrate and leachate are combined and this organic phase is extracted with several amounts of a 2% aqueous solution of sulfuric acid until the Mayer test, which discloses the presence of alkaloids, is negative on the last acid liquors. After decantation, the aqueous phase is recovered and rendered alkaline with aqueous ammonia in the presence of chloroform. A further decantation is carried out to recover on the one hand the organic phase and on the other hand the aqueous phase, which is extracted with chloroform until a Mayer test is practically negative on the last alkaline liquors. The chloroform phases are washed with water and then combined and dried over anhydrous sodium sulfate. This chloroform solution is then distilled to recover 6.5 g of a mixture of tertiary bases containing mainly oxyacanthine (about 50%) and berbamine. Thus the yield is about 1.3% based on the initial dry matter.

If desired, the oxyacanthine can be separated from the other tertiary bases by a known separation technique, reference being made in particular to the publication by A. ORECHOW, Archiv der Pharmazie (1933) 271, 323–7.

The present invention is preferably carried out using the above-mentioned mixture of bases in the form of a mixture of sulfates, which is obtained by the following method.

The mixture of tertiary bases obtained above is dissolved in an amount of acetone which is just sufficient. This solution is acidified to pH 3 with concentrated sulfuric acid. The bases then precipitate in the form of sulfates. After filtration, the precipitate is dissolved in methanol and the solution is then evaporated to dryness to give about 6.7 g of a mixture of sulfates of tertiary bases, including oxyacanthine sulfate. In the remainder of the description and the drawings, this mixture will be referred to as the "sulfate extract" of *Berberis vulgaris*.

EXAMPLE 2

Preparation of an extract of root barks of *Berberis vulgaris* by extraction with alcohol 200 g of dried and finely ground root barks of *Berberis vulgaris* are placed in a round-bottomed flask, about 2 l of methanol are added and the mixture is refluxed for 2 h. It is left to cool to room temperature and filtered. The methanol is then distilled to recover about 12 g of extract having an oxyacanthine content of about 2%.

Extracts can be obtained analogously with other parts of the plant, in particular the stems, and with other solvents, such as ethyl acetate or an aqueous-alcoholic mixture containing 30% of ethanol. In the case of extraction with 30% ethanol, the solution containing the extract is concentrated by distillation under reduced pressure and then lyophilized at −80° C. The mean extraction yields based on the initial dry matter, and the oxyacanthine contents of the extract, are collated in Table I below.

TABLE I

| Parts of the plant | Extraction yield | | | Oxyacanthine content | | |
| --- | --- | --- | --- | --- | --- | --- |
| | methanol | 30% ethanol | ethyl acetate | methanol | 30% ethanol | ethyl acetate |
| roots | 6% | 10% | | 2% | 3–4% | |
| stems | 5% | | <1% | 1% | | 2% |

EXAMPLE 3

Preparation of a composition according to the invention comprising a mixture of sulfate of tertiary bases from

*Berberis vulgaris*, associated with a mixture of saponins from *Medicago sativa*

A—Preparation of a mixture of saponins from roots of lucerne (*Medicago sativa*)

1 kg of powdered lucerne roots is taken and macerated in 6 l of methanol for 2 h. The suspension is refluxed for 3 h. After cooling, it is filtered and the residue is resubjected to the above treatment with fresh methanol. The operation is repeated 3 times. The methanol phases are combined and evaporated under vacuum. The residue is stirred with 200 ml of ethyl ether. The material insoluble in ether is recovered by filtration and dissolved in 3 l of water and the solution is extracted with normal butanol saturated with water (3 l then 2×2 l).

The butanol phases are combined and evaporated under vacuum.

The residue (about 150 g) is dissolved in 1.5 l of water and dialyzed against pure water for 4 days, the water being renewed daily. The contents of the dialysis cell are lyophilized.

An additional purification is advantageously carried out: the lyophilizate is dissolved in 300 ml of methanol and discharged into 1.5 l of ether. The precipitate, consisting of the mixture of saponins, is recovered by filtration and dried overnight under vacuum, in the presence of $P_2O_5$. The mean yield is 30 g.

B—Preparation of the composition according to the invention 0.1 g of a mixture of sulfates of tertiary bases from root cortices of Berberis, prepared according to Example 1, and 0.1 g of a mixture of saponins from lucerne, obtained in the previous step, are dissolved successively in an excipient (EX) of the following composition: propylene glycol 20%, ethanol 63%, water 17%.

This gives a composition according to the invention which can be used as such for application to the scalp, in particular for retarding hair loss, stimulating hair growth or combating itching.

EXAMPLE 4

Process for the preparation of methyloxyacanthine hydrochloride

Methylation is carried out on oxyacanthine base.

Starting from 840 mg of sulfate, the oxyacanthine is extracted from its salt with $CHCl_3$ (4×100 ml) in an alkaline medium (NaOH).

After washing with water, drying over $Na_2SO_4$ and evaporation of the $CHCl_3$ under reduced pressure at 40° C., the base obtained weighs about 706 mg. The yield is 97%.

The oxyacanthine base is methylated with diazomethane by dissolving the base in 30 ml of methanol, cooling to 0° C. and then gradually adding 20 ml of an ethereal solution of diazomethane containing 3 g/l.

The reaction, which is monitored by thin layer chromatography, is continued for 24 h at 0° C.

The methylation is confirmed by NMR.

The hydrochloride is then prepared by concentrating the methanol solution of the methylated product to about 10 ml under reduced pressure. This is followed by the addition of 1.1 ml of a methanol/2N HCl mixture, after which the hydrochloride salt is precipitated by the addition of 50 ml of dry ether.

The precipitates obtained after filtration are washed with cold acetone.

After evaporation of the acetone, 653 mg of hydrochloride salt are obtained which, when added to the lyophilization of the mother liquors, give an additional 95 mg, i.e. a total of 748 mg of the hydrochloride salt of methyloxyacanthine, corresponding to a yield of 92%.

EXAMPLE 5

Incorporation of a mixture of sulfates of tertiary bases from root barks of *Berberis vulgaris* into hydrated lipidic lamellar phases or into liposomes A mixture of sulfates of tertiary bases from root barks of *Berberis vulgaris*, obtained according to Example 1, is incorporated into hydrated lipidic lamellar phases or into liposomes by the following preparative technique:

The following are weighed out:

soya lecithin: 18 g

β-sitosterol: 2 g mixture of sulfates of tertiary bases of Example 1: 1 g

These constituents are dissolved in a mixture consisting of 300 ml of dichloromethane.

The resulting mixture is evaporated in a round-bottomed flask on a rotary evaporator at a temperature of 45° C.

The lipidic film thus obtained is then taken up and dispersed in distilled water qsp 750 g at room temperature for 12 h, with stirring.

The resulting suspension of lipidic vesicles is then homogenized by treatment with ultrasound for 15 min at 4° C., at a power of 200 W, in 150 ml fractions.

The mean size of the liposomes thus obtained is 134.4±8.4 nanometers.

In one advantageous variant, this suspension is then gelled by being mixed with 250 g of 1.25% Carbopol® 980 gel, separately prepared in conventional manner.

This gives about 1000 g of a gelled suspension of liposomes encapsulating the mixture of sulfates of tertiary bases, the concentration of which is about 0.1% based on the total weight of the suspension.

This gel is called "composition $I_6$" and can be used as such within the framework of the invention.

EXAMPLE 6

Demonstration of the activity of oxyacanthine, used by itself or in association with a saponin, on the pilary system The test is based on a study of the activity of the products according to the invention on the pilary cycle of Sprague Dawley rats, all 23 d old (d=day). The pilary cycles of all the animals are still synchronous at this age.

The aim is more particularly to demonstrate the activity of these products on the prolongation of the hair growth phase or so-called "anagenic phase".

The first step is to determine which day corresponds to the maximum number of hairs in the anagenic phase during the second pilary cycle, starting between d 32 and 35 of the animals' life.

This is done in the following manner. On d 24, the rats are shaved on the sides of the lower part of the back so as to leave only a short length of hairs which is just enough to allow subsequent depilation. At substantially regular intervals of time (about every 2 or 3 d), starting from d 28, a tuft of hairs is removed from the animal's left side using tweezers. The roots of 10 hairs selected at random from this tuft are observed under high magnification and the number of hairs in the anagenic phase, recognizable by the characteristic shape of the root, is counted. The percentage of hairs in the anagenic phase is thus determined as a function of time.

This determination is performed on a group of 10 animals for each of the three series of experiments which are to be described below. For these three groups, Table II below gives the mean percentages of hairs in the anagenic phase as a function of the age expressed in days.

TABLE II

| | Age (days) | | | | | | | | | | |
|---|---|---|---|---|---|---|---|---|---|---|---|
| | 28 | 30 | 32 | 35 | 37 | 39 | 42 | 44 | 46 | 49 | 51 |
| 1st group | 0 | 0 | 0 | 0 | 15 | 100 | 100 | 94 | 6 | 0 | 0 |
| 2nd group | 0 | 0 | 0 | 0 | 27 | 98 | 85 | 80 | 39 | 0 | 0 |
| 3rd group | 0 | 0 | 0 | 86 | 89 | 93 | 84 | 71 | 28 | 0 | 0 |

These results show that the anagenic phase reaches its maximum on d 39 with a value close to 100%. Thus, on this day, practically all the hairs of all the animals are in the growth phase. The number of hairs in the anagenic phase then decreases to reach a value of zero on about d 49.

To demonstrate the prolongation of the anagenic phase, it will then be necessary only to observe the slowing-down of the decrease in the number of hairs in the anagenic phase as from d 39 of the animals' life.

The present study relates to the following products:

product $I_1$: Commercial oxyacanthine sulfate at a concentration of 0.1% in the excipient EX described in Example 3B, product $I_2$: "Sulfate extract" of *Berberis vulgaris* according to Example 1 at a concentration of 0.1% in the excipient EX, product $I_3$: Commercial oxyacanthine sulfate at a concentration of 0.1% and a mixture of saponins from lucerne roots according to Example 3A at a concentration of 0.1% in the excipient EX, product $I_4$: Composition according to Example 3B ("sulfate extract" of *B. vulgaris* at a concentration of 0.1% and a mixture of saponins from lucerne according to Example 3A at a concentration of 0.1% in the excipient EX), product $I_5$: Composition analogous to that of Example 3B except that the respective concentrations are 0.18% for the "sulfate extract" and 0.09% for the mixture of saponins, the composition of the excipient being identical, and product EX: Excipient EX as described in Example 3B.

The products $I_1$ to $I_5$ are products according to the invention; the product EX is a control product.

Three series of experiments were performed in order to test the above-mentioned products.

The animals are shaved on d 24, as indicated above. The test products are applied to the shaved part of the back from d 25 to d 65, 6 d out of 7, at a dose which changes with the weight of the animals. This dose is 0.5 ml on d 25 and reaches 2 ml on d 65.

In each of these series of experiments, the percentage of hairs in the anagenic phase is determined as above.

Series 1 is carried out on 40 animals divided into 4 groups of 10 animals. The first group, which receives the product EX, is designated by the expression "excipient control". Groups 2, 3 and 4 receive the products $I_2$, $I_3$ and $I_4$ respectively. The results are shown in Table III and FIGS. 1, 3 and 2.

Series 2 is carried out on 20 animals divided into 2 groups of 10 animals. The first group is the "excipient control" group. The second group receives the product $I_1$. The results are shown in Table IV and FIG. 4.

Figure 5:
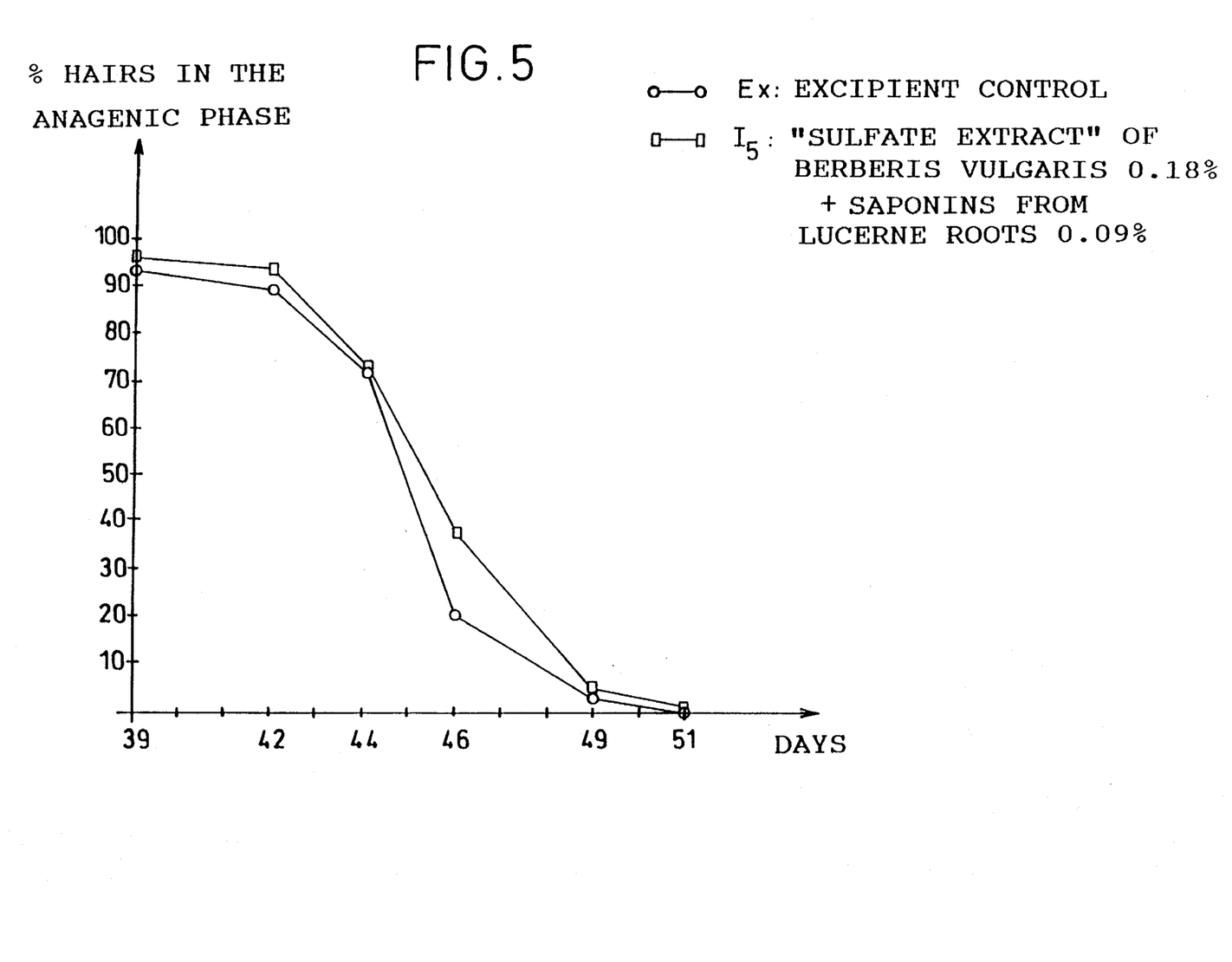
FIG. 5 is similar to FIG. 2 except that the concentrations of the constituents of the composition are respectively 0.18% for the mixture of sulfates of tertiary bases and 0.09% for the mixture of saponins.

Series 3 is also carried out on 20 animals divided into 2 groups: an "excipient control" group and a group receiving the product $I_5$. The results are shown in Table V and FIG. 5.

The results of this trichokinetic study (trichogram as a function of time) are shown as mean values in FIGS. 1 to 5 attached, in which the percentage of hairs in the anagenic phase has been shown on the ordinate and the time, between day 39 and day 51 of the animals' life, has been shown on the abscissa. Tables III to V below give the values of the areas under the curves obtained between d 39 and d 51 (S). The activity, measured relative to the excipient serving as a reference control, is determined for each area value. In fact, it is seen that, over a given period, the area between a curve and the abscissa axis is proportional to the quantity of hairs in the anagenic phase. Thus the determination of this area under each curve allows a quantitative comparison of the activity of the products, as regards the increase in the proportions of hairs in the anagenic phase, relative to one another and/or relative to the controls.

As the maximum proportion of hairs in the anagenic phase in the "absolute control" group occurs on about day 39, determination of the area under the curve as from this day makes it possible to assess the effect of each product on the prolongation of the anagenic phase, especially relative to the controls.

ACTIVITY OF THE PRODUCTS OF THE INVENTION

Comparison of the areas under the curves

S: area under the curve (expressed in %×day) corresponding to the products $I_1$ to $I_5$ or to the excipient EX between day 39 and day 51

$T_e$: excipient control EX $P_a$: percentage prolongation of the anagenic phase (relative to the excipient control)

$$P_a = \frac{S_I - S_{EX}}{S_{EX}} \times 100$$

TABLE III

| $T_c$ | $I_2$ (FIG. 1) | $I_4$ (FIG. 2) | $I_3$ (FIG. 3) |
|---|---|---|---|
| S 620.5 | 638 | 667.5 | 677.5 |
| $P_a$ % 0 | 2.8 | 7.6 | 9.2 |

TABLE IV

| | $T_c$ | $I_1$ (FIG. 4) |
|---|---|---|
| S | 639 | 657 |
| $P_a$ % | 0 | +2.8 |

TABLE V

| | $T_c$ | $I_5$ (FIG. 5) |
|---|---|---|
| S | 563 | 625.5 |
| $P_a$ % | 0 | 11.1 |

Figure 1:
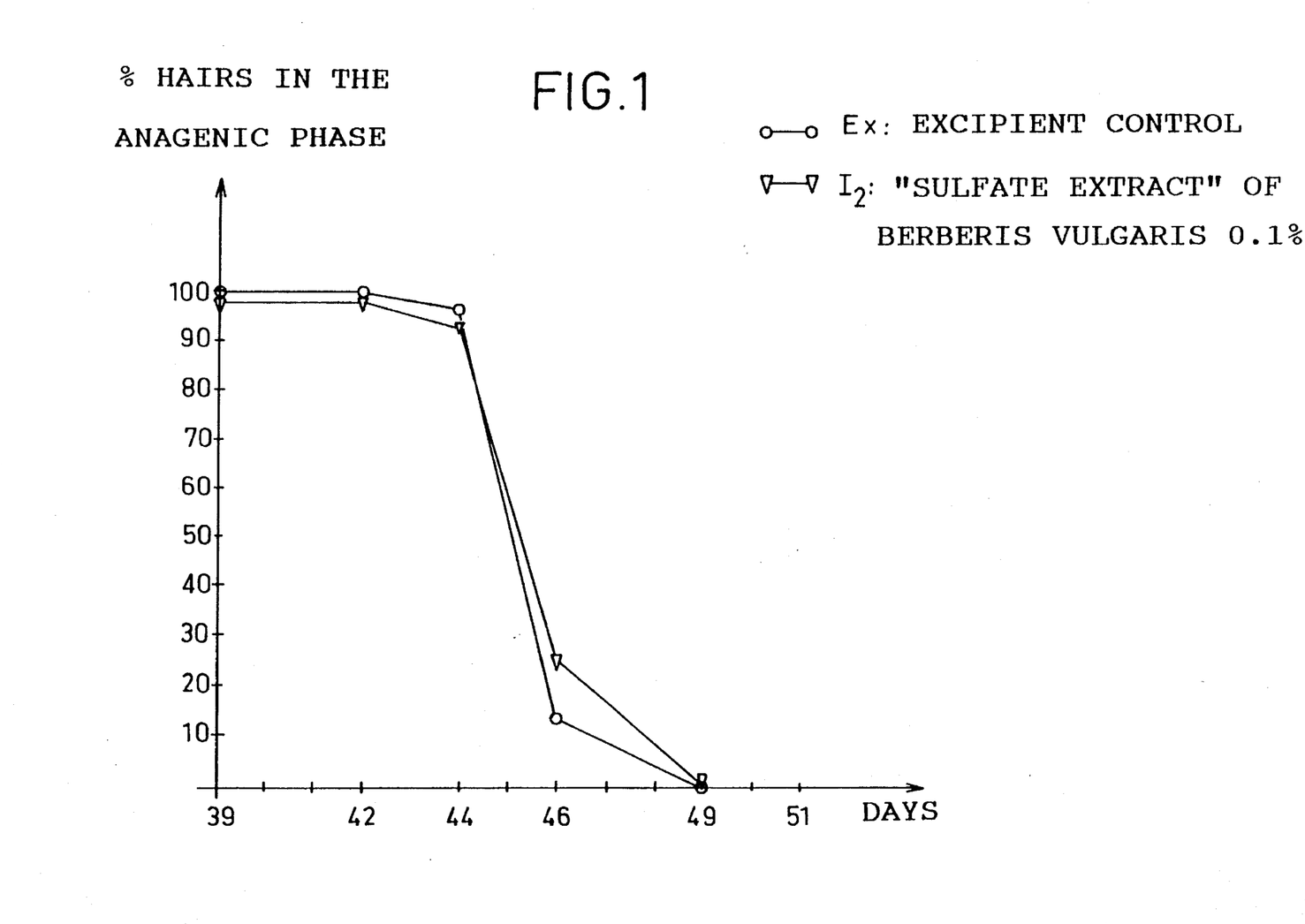
FIG. 1 reports results of comparative experiments based on a trichokinetic study relating to the pilary system of the Sprague Dawley rat, with a composition containing 0.1% of a mixture of sulfates of tertiary bases from *Berberis vulgaris*, including oxyacanthine sulfate, compared with an excipient control. The percentage of hairs in the anagenic phase has been shown on the ordinate and the number of days on the abscissa.
Figure 2:
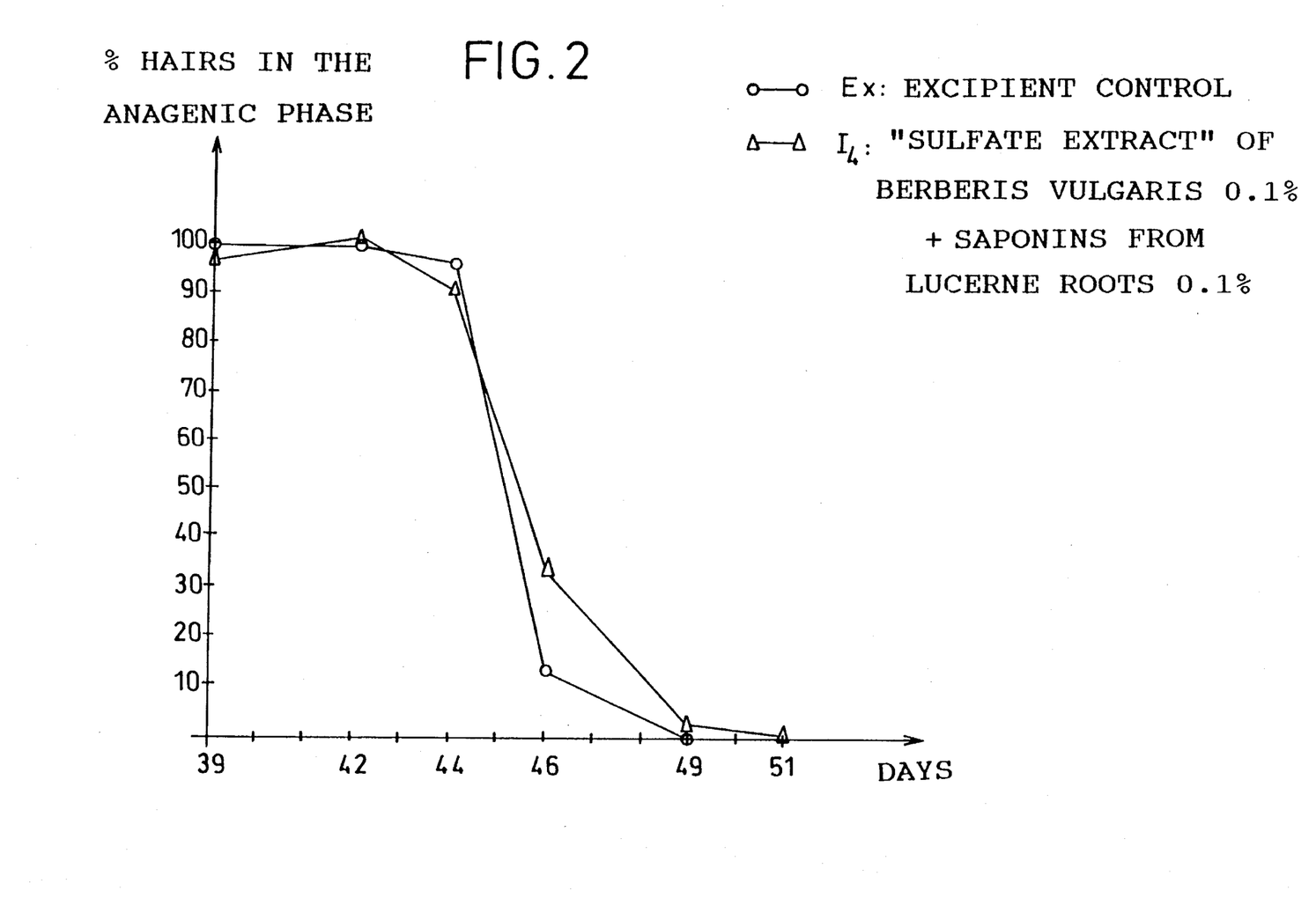
FIG. 2 is similar to FIG. 1 but relates to a composition containing 0.1% of the above-mentioned mixture of sulfates of tertiary bases, associated with 0.1% of a mixture of saponins extracted from *Medicago sativa*.
Figure 3:
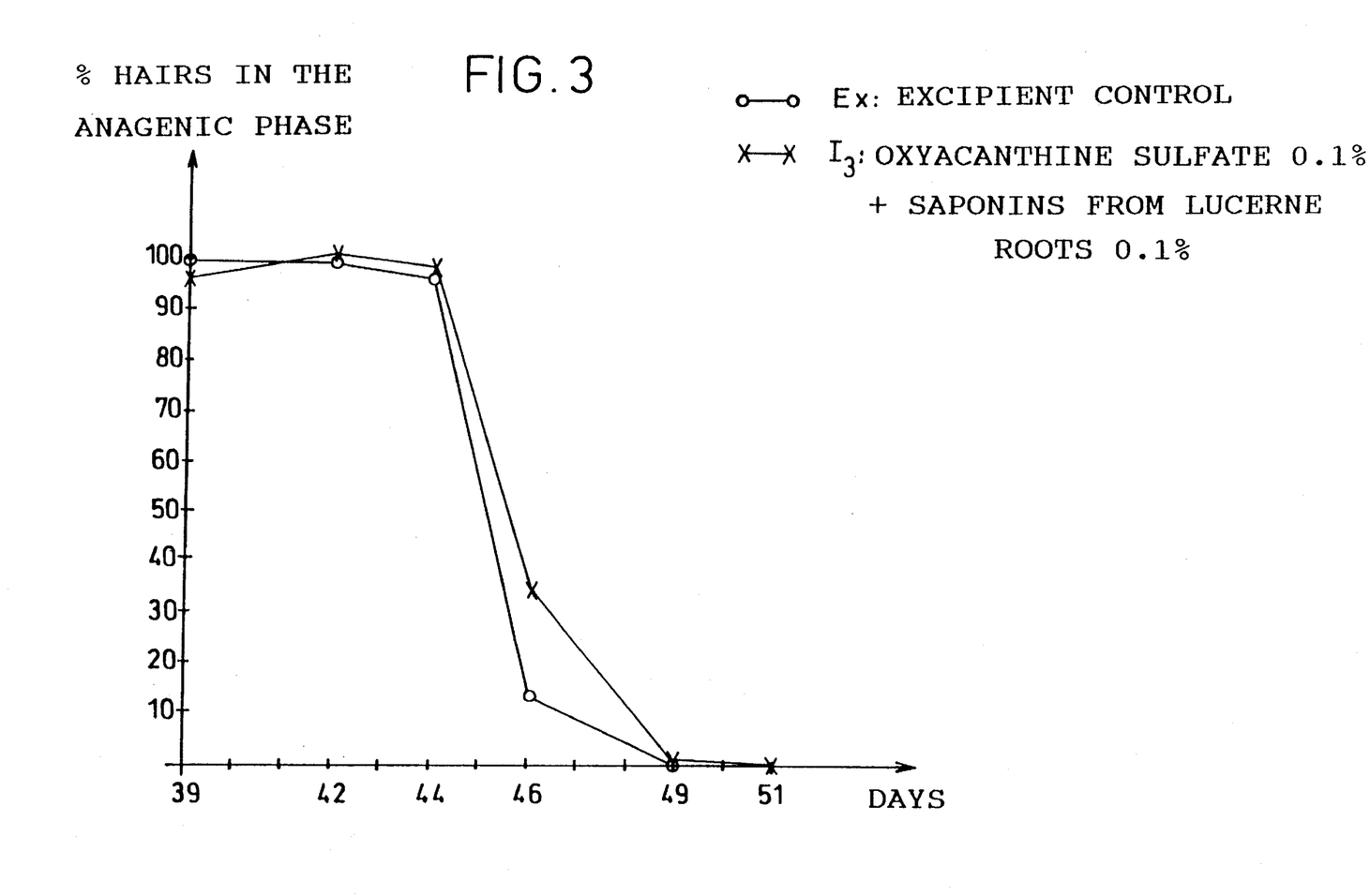
FIG. 3 shows similar curves to those of FIG. 1 and is based on the results obtained with a composition comprising 0.1% of commercial oxyacanthine sulfate associated with 0.1% of the above-mentioned mixture of saponins.
Figure 4:
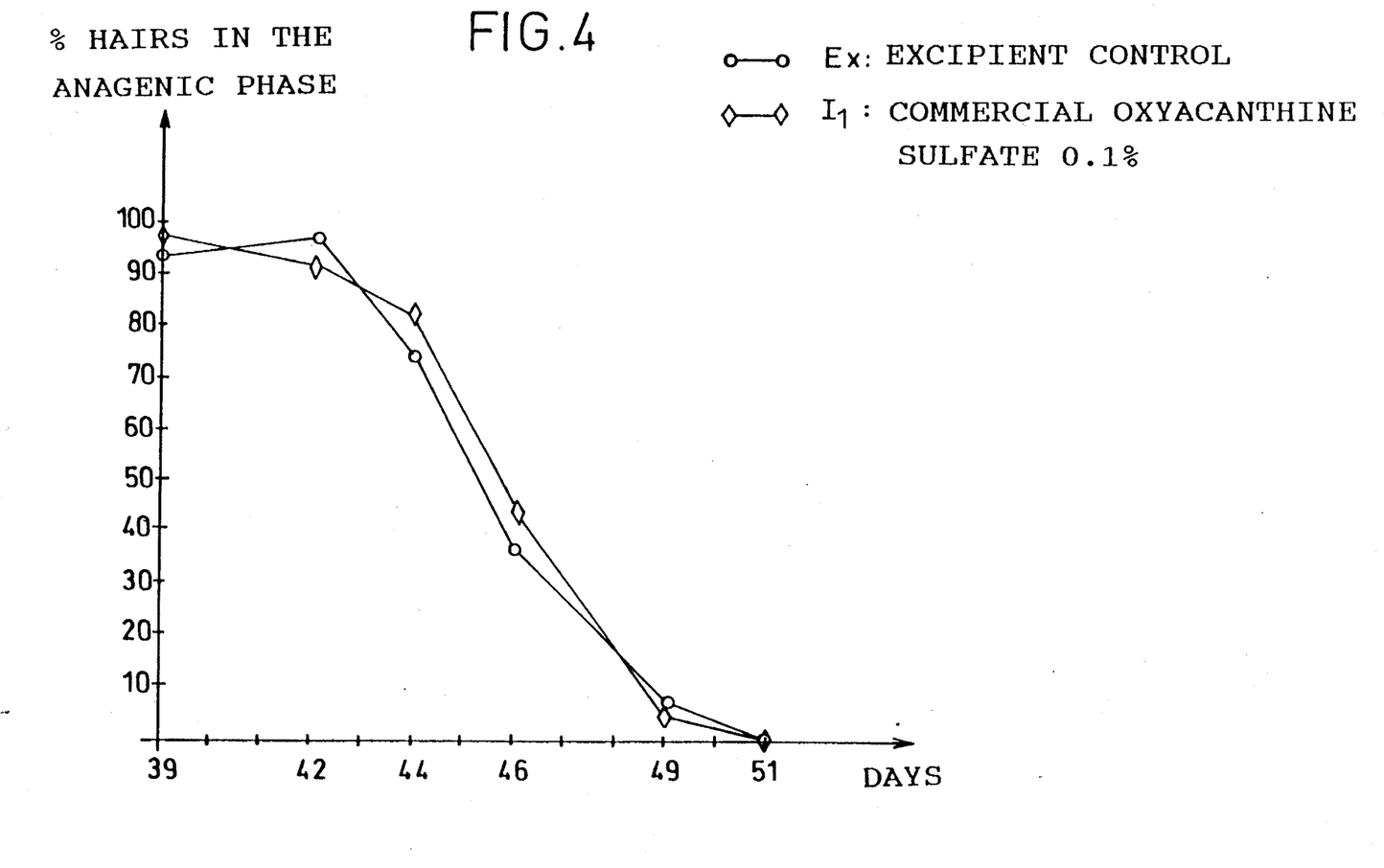
FIG. 4 is similar to FIG. 1 but relates to a composition containing 0.1% of commercial oxyacanthine sulfate.

In FIGS. 1 to 5 attached, the curves joining the white circles correspond to the results obtained with the control excipient. In FIG. 1, the curve joining the downward-pointing triangles corresponds to the use of the preparation $I_2$, which only contains the "sulfate extract" of *Berberis vulgaris* at a concentration of 0.1% in the excipient. In FIG. 2, the curve joining the upward-pointing triangles relates to the preparation $I_4$, which contains the "sulfate extract" of *B. vulgaris* at a concentration of 0.1% in association with the saponins from lucerne roots according to Example 3A at a concentration of 0.1% in the excipient. In FIG. 3, the curve joining the crosses is obtained with the product $I_3$, which contains commercial oxyacanthine sulfate at a concentration of 0.1% in association with the saponins from lucerne roots at a concentration of 0.1% in the excipient. In FIG. 4, the curve joining the diamonds corresponds to the use of the preparation $I_1$, which only contains commercial oxyacanthine sulfate at a concentration of 0.1% in the excipient. Finally, in FIG. 5, the curve joining the squares relates to the composition $I_5$, which contains the "sulfate extract" of *Berberis vulgaris* at a concentration of 0.18% in association with the saponins from lucerne roots according to Example 3A at a concentration of 0.09%.

Tables III to V show that, relative to the controls, the area S representing the proportion of hairs in the anagenic phase (growth phase) increases substantially with the products of the invention containing the "sulfate extract" of *Berberis vulgaris*, including oxyacanthine sulfate, this phenomenon being all the more pronounced when this extract or the oxyacanthine sulfate is associated with the saponins from lucerne. Moreover, FIGS. 1 to 5 clearly show that all the products of the invention which were tested prolong the growth phase of the hairs (anagenic phase), since it is observed with time that the percentage of anagenic hairs is higher than for the control animals, i.e. that there is a slowing-down of the decrease in the number of anagenic hairs, and that there is a non-zero percentage for a longer time.

Thus these experiments clearly demonstrate that, by increasing the duration of the anagenic phase, oxyacanthine, by itself or combined with at least one saponin, very appreciably retards hair loss, which constitutes a particularly unexpected property.

EXAMPLE 7

Demonstration of the activity of a mixture of sulfates of tertiary bases from root barks of *Berberis vulgaris*, incorporated into liposomes, compared especially with minoxidil The same protocol as in the previous Example is used on Sprague Dawley rats, all 23 d old (d=day).

In the present experiment, however, doubtless because of the different period of the year at which it was carried out, the day corresponding to the maximum number of hairs in the anagenic phase is d 42.

The present study relates to the following products:

product $I_2$: "sulfate extract" of *Berberis vulgaris* according to Example 1 at a concentration of 0.1% in the above-mentioned excipient EX, product $I_6$: gel containing the "sulfate extract" of *Berberis vulgaris* incorporated into liposomes according to Example 5, comparative product L: liposomal gel prepared according to Example 5 except that it does not contain any active substance according to the invention, and comparative product M: minoxidil (positive control) at a concentration of 2% in the above-mentioned excipient EX.

The study is performed on 50 animals divided into 5 groups of 10 animals.

The first and second groups receive the products $I_2$ and $I_6$ according to the invention, respectively. The third group receives the product L, the fourth receives the product M and the fifth, namely the control group T, does not receive any product. The results are shown in Table VI and FIGS. 6 and 7 in a presentation analogous to that of the results of the study of the previous Example.

ACTIVITY OF THE PRODUCTS OF THE INVENTION

Comparison of the areas under the curves

S: area under the curve (expressed in %×day) corresponding to the products $I_2$, $I_6$, L and M and to the curve of the control group T, from day 42 to 53

$P_{aT}$: percentage prolongation of the duration of the anagenic phase (relative to the control T)

$$P_{aT} = \frac{S_I - S_T}{S_T} \times 100$$

$A_M$: activity on the prolongation of the duration of the anagenic phase relative to minoxidil, the positive control $$A_M = \frac{S_I}{S_M} \times 100$$

TABLE VI

|  | T control group | L | $I_2$ | $I_6$ | M |
|---|---|---|---|---|---|
| S | 625.5 | 643.5 | 636 | 674.5 | 520 |
| $P_{aT}$ | 0 | 3.20 | 1.68 | 7.83 | −16.90 |
| $A_M$ | 120 | 124 | 122 | 130 | 100 |

Figure 6:
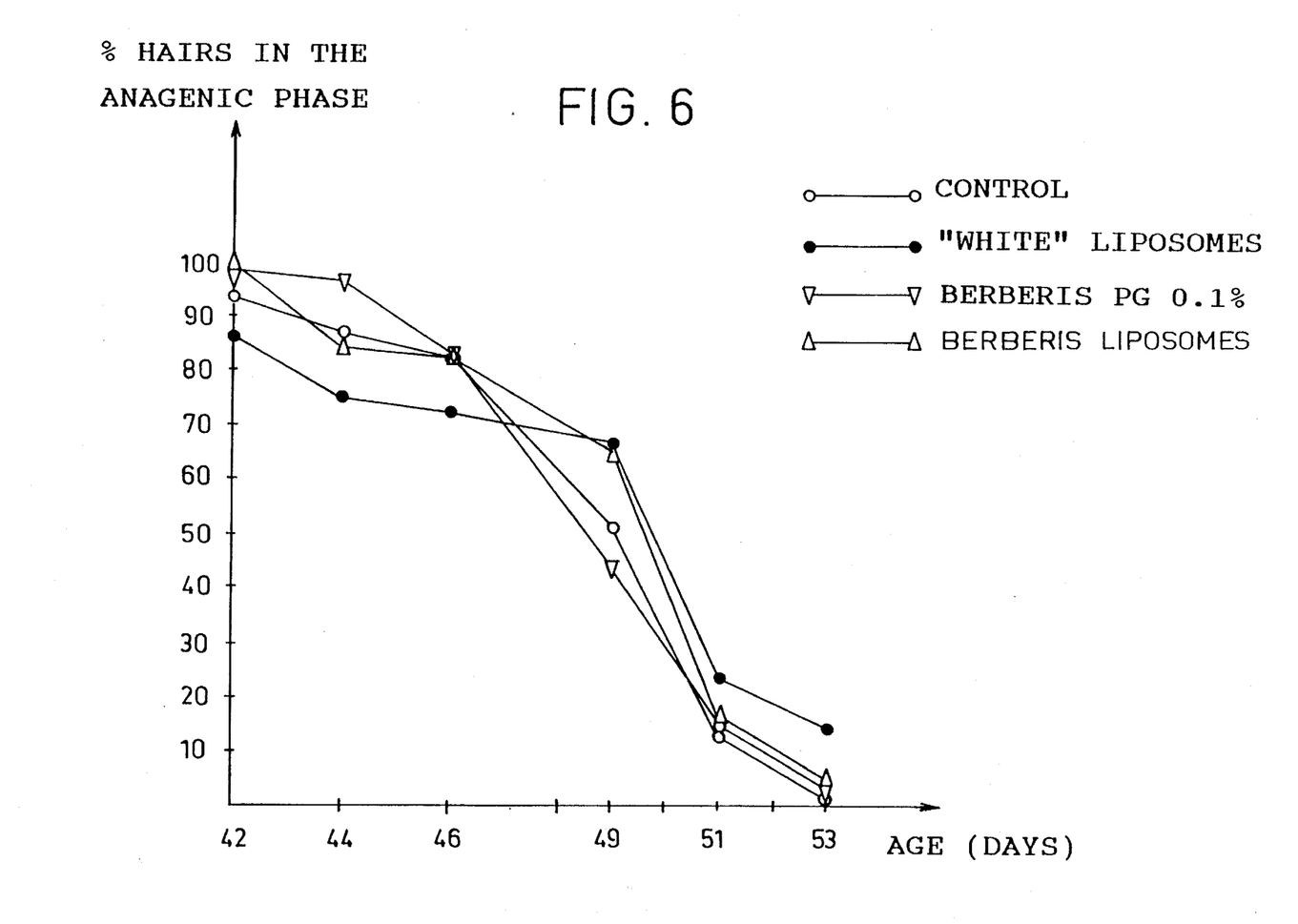
FIG. 6 is similar to FIG. 1 except that the comparison relates to an extract of Berberis in the free state, an extract of Berberis encapsulated in a liposome, and empty liposomes, called "white" liposomes, compared with a control.
Figure 7:
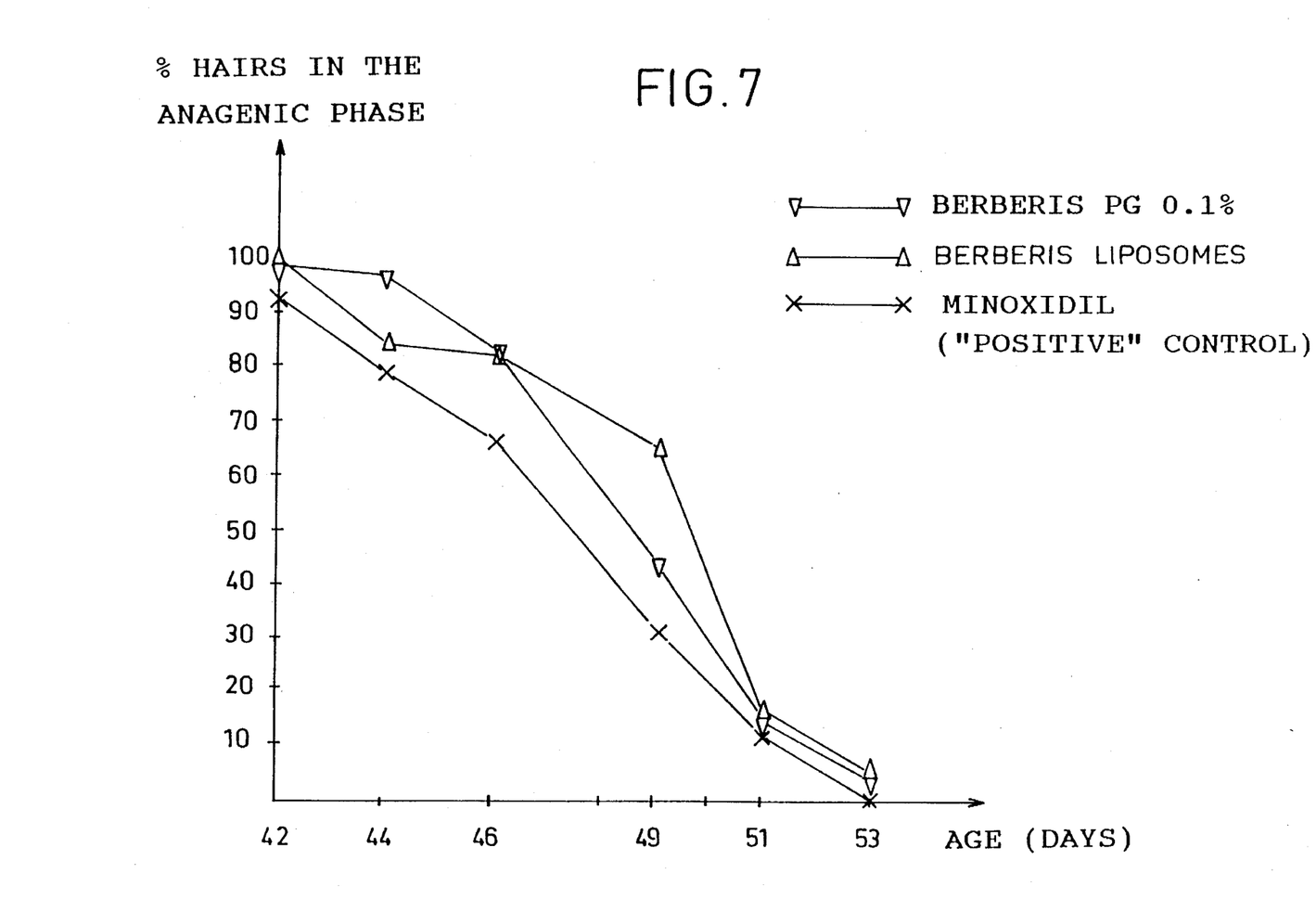
FIG. 7 is similar to FIG. 6 and shows the curves for the extract of Berberis in a liposome and the extract of Berberis in the free state, compared with minoxidil used as a "positive" control.

In FIGS. 6 and 7 attached, the curves joining the downward-pointing triangles relate to the results for the product $I_2$, i.e. the "sulfate extract" of Berberis vulgaris at a concentration of 0.1% in the excipient EX, and those joining the upward-pointing triangles relate to the results for the product $I_6$, i.e. the liposomal gel incorporating the "sulfate extract" of *Berberis vulgaris*. In FIG. 6, the curve joining the white circles corresponds to the results for the control group T and the curve joining the black circles corresponds to the results for the comparative product L, i.e. the above-mentioned liposomal gel. In FIG. 7, the curve joining the crosses corresponds to the results for the comparative product M, i.e. minoxidil at a concentration of 2% in the excipient EX.

Table VI shows that, relative to the control group, anagenic phase is prolonged substantially, not only in the groups which have received the products of the invention $I_2$ and $I_6$, but also in the group which has received the product L, i.e. the liposomal gel (empty or so-called "white" liposomes). The latter observed phenomenon is doubtless due to the intrinsic activity of the liposomes prepared by the above-described method, at the hair follicles, on the growth of the hair. On the other hand, there is a clearly apparent synergy between the liposomes and the "sulfate extract" when the latter is incorporated, since the percentage prolongation of the anagenic phase $P_{aT}$ for the product $I_6$ is very considerably greater than the sum of those corresponding to the product L and the product $I_2$ respectively.

Furthermore, the results obtained for the activity $A_M$ relative to minoxidil show that the activity of the products of the invention is very considerably greater. It seems in fact that minoxidil exhibits no action on the prolongation of the anagenic phase quite the reverse. However, the results of our study over the period preceding d 42, which are not reported here, shows a very much greater activity of minoxidil at the start of this phase, i.e. a high activity on the stimulation of hair regrowth.

Thus these experiments clearly demonstrate on the one hand that plant extracts containing oxyacanthine incorporated into liposomes have an improved activity in retarding hair loss by increasing the duration of the anagenic phase to a greater extent than in the case where these extracts are not incorporated, and on the other hand that the products of the present invention possess a greater activity than that of minoxidil in this application, which constitutes a particularly unexpected advantage.

Various Examples of formulations of cosmetic compositions will be given below.

EXAMPLE 8

Hair lotion for retarding hair loss

| | |
|---|---|
| 30% aqueous-ethanolic extract of root barks of Berberis vulgaris according to Example 2 | 0.05 g |
| saponins from lucerne roots according to Example 3A | 0.05 g |
| Ceraphyl 60 ® | 0.10 g |
| absolute ethanol | 25.00 g |
| Phenonip ® | 0.40 g |
| Cremophor RH40 ® | 0.50 g |
| perfumed aqueous excipient | qsp 100.00 g |

EXAMPLE 9

Hair tonic lotion for combating hair loss

| | |
|---|---|
| oxyacanthine sulfate | 0.10 g |
| saponins from lucerne roots according to Example 3A | 0.10 g |
| BHA | 0.05 g |
| Ceraphyl 60 ® | 0.09 g |
| Cremophor RH40 ® | 0.50 g |
| ethanol | 32.00 g |
| water + perfume | qsp 100.00 g |

EXAMPLE 10

Hair stimulating and styling lotion for combating hair loss

| | |
|---|---|
| "sulfate extract" of Berberis vulgaris according to Example 1 | 0.20 g |
| saponins from lucerne roots according to Example 3A | 0.20 g |
| Ceraphyl 60 ® | 0.10 g |
| ethanol | 40.00 g |
| BHA | 0.01 g |
| propylene glycol | 4.00 g |
| Cremophor RH40 ® | 0.50 g |
| water + perfume | qsp 100.00 g |

EXAMPLE 11

Hair treating gel for prolonging the growth phase of the hair

| | |
|---|---|
| "sulfate extract" of Berberis vulgaris according to Example 1 | 0.05 g |
| saponins from lucerne roots according to Example 3A | 0.02 g |
| ethanol | 30.00 g |
| Cremophor RH40 ® | 0.50 g |
| 2% Carbopol 980 ® gel | 50.00 g |
| water | qsp 100.00 g |

EXAMPLE 12

Hair lotion for combating pruritus

| | |
|---|---|
| 30% aqueous-ethanolic extract of stems of Berberis vulgaris according to | 0.15 g |
| Example 2 | |
| Ceraphyl 60 ® | 0.15 g |
| ethanol | 30.00 g |
| Phenonip ® | 0.40 g |
| ethoxylated hydrogenated castor oil | 0.50 g |
| perfumed aqueous excipient | qsp 100.00 g |

EXAMPLE 13

Emulsion for soothing the skin

| Phase A | |
|---|---|
| Tefose 1500 ® | 7.00 g |
| cetyl alcohol | 2.00 g |
| paraffin oil | 20.00 g |
| squalane | 5.00 g |
| Phase B | |
| Cremophor RH40 ® | 0.50 g |
| 30% aqueous-alcoholic extract of stems of B. vulgaris | 0.10 g |
| Phase C | |
| 2.5% Carbopol 980 ® gel | 12.00 g |
| Phase D | |
| Germaben II ® | 0.8 g |

The extract of stems of Berberis is solubilized in the Cremophor RH40® with heating, water is added and the whole is heated to 80° C.

Phase A, heated to 80° C. beforehand, is incorporated into the above phase. The mixture is homogenized. Phase C is then incorporated at 60° C., with homogenization, the mixture is then left to cool to 40° C. and phase D is incorporated. Finally, homogenization of the emulsion is maintained for about 1 h until room temperature is reached.

EXAMPLE 14

Emulsion for soothing the skin

| Phase A | |
|---|---|
| Cremophor A6 ® | 2.00 g |
| Cremophor A25 ® | 2.00 g |
| glycerol monostearate | 3.00 g |
| cetyl alcohol | 3.00 g |
| paraffin oil | 6.00 g |
| sweet-almond oil | 6.00 g |
| squalane | 2.20 g |
| Phase B | |
| 30% aqueous-ethanolic extract of root bark of B. vulgaris | 0.10 g |
| methyl p-hydroxybenzoate | 0.15 g |
| glycerol | 4.00 g |
| water | 71.55 g |

Phases A and B are heated separately to 80° C.

When these phases are homogeneous, phase B is incorporated into phase A at the same temperature, with stirring, and stirring is maintained until the emulsion has returned to room temperature, i.e. for about 1 h to 1 h 30 min.

EXAMPLE 15

Hair lotion for combating hair loss

| | |
|---|---|
| methyloxyacanthine hydrochloride prepared according to Example 4 | 0.05 g |
| propylene glycol | 10 g |
| 95% ethyl alcohol | 30 g |
| perfumed aqueous excipient | qsp 100 g |

EXAMPLE 16

Dermo-cosmetic composition "Duo" for slowing down hair loss and stimulating hair regrowth This "duo" is presented in the form of two products, A and B, which are separately packaged in two containers placed side-by-side, but are mixed immediately before use. Examples of devices which can be used for this purpose are that based on the principle of the one described in the document FR-A-2 603 558, corresponding to U.S. Pat. No. 4,773,562, or that marketed by VALOIS-France under the name DUOPACK®.

Product A:

Liposomal gel incorporating a mixture of sulfates of tertiary bases from root barks of *Berberis vulgaris* according to Example 5, to which preservatives and perfumes can be added . . . 30 ml.

Product B:

| 10 ml of the following composition: | |
|---|---|
| minoxidil | 8% |
| propylene glycol | 20% |
| 95% ethanol | 63% |
| perfumed aqueous excipient qsp 100% | 10 ml |

The device is preferably constructed so as to dispense simultaneously at least 3 volumes of product A per volume of product B; in this way, the concentration of the alcoholic excipient of B is not such as to destabilize the liposomes of A.

This "duo" is preferably used as an intensive treatment at a rate of one application to the scalp morning and evening for 3 months.

What is claimed is:

1. A method of promoting hair growth, for delaying hair loss, and for combating pruritus associated with an area of the body selected from the group consisting of hair and scalp, said method comprising the topical application to said hair and scalp in an amount effective for achieving said desired effect, of an active ingredient consisting essentially of at least one oxyacanthine component selected from the group consisting of:

a) an oxyacanthine of formula (I) below:

wherein R is hydrogen (oxyacanthine), a $C_1$–$C_{12}$ hydrocarbon chain, or a $C_2$–$C_{12}$ acyl radical, said hydrocarbon chain being selected from the group consisting of a saturated radical, an unsaturated radical, a linear radical, a branched radical, and a cyclic radical, said acyl radical being selected from the group consisting of a saturated radical, an unsaturated radical, a linear radical, a branched radical, and a cyclic radical, and b) an acid addition salt of said oxyacanthine of formula (I) defined under a), said oxyacanthine being present in a concentration of at least 0.001% by weight with respect to the total weight of said composition.

2. The method of claim 1, wherein said oxyacanthine component is oxyacanthine.

3. The method of claim 1, wherein R is selected from the group consisting of a methyl, hexyl, decyl, acetyl, propanoyl, butanoyl, hexanoyl and octanoyl radical.

4. A method of promoting hair growth, for delaying hair loss, and for combating pruritus associated with an area of the body selected from the group consisting of hair and scalp, said method comprising the topical application to hair and scalp in an amount effective for achieving said desired effect, of an active ingredient consisting essentially of at least one oxyacanthine component selected from the group consisting of:

a) an oxyacanthine of formula (I) below:

wherein R is hydrogen (oxyacanthine), a $C_1$–$C_{12}$ hydrocarbon chain, or a $C_2$–$C_{12}$ acyl radical, said hydrocarbon chain being selected from the group consisting of a saturated radical, an unsaturated radical, a linear radical, a branched radical, and a cyclic radical, said acyl radical being selected from the group consisting of a saturated radical, an unsaturated radical, a linear radical, a branched radical, and a cyclic radical, and b) an acid addition salt of said oxyacanthine of formula (I) defined under a), said oxyacanthine component being combined with one saporin.

5. The method of claim 1, wherein said oxyacanthine component of formula (I) is sulfuric acid addition salt.

6. The method of claim 1, wherein the concentration of said oxyacanthine component ranges between 0.001% and 5% by weight based on total weight of said composition.

7. The method of claim 1, wherein the concentration of said oxyacanthine component ranges between 0.01% and 2% by weight based on the total weight of said composition.

8. The method of claim 4, wherein said saponin is selected from the group consisting of steroid saponins, triterpene saponins and mixtures thereof.

9. The method of claim 8, wherein said steroid saponin is selected from the group consisting of saponins having diosgenin structures and saponins having sarsapogenin structures; wherein said triterpene saponin is selected from the group of saponins having oleanane structure and sapogenins having ursane structure.

10. The method of claim 9, wherein said saponin having an oleanane structure is selected from the group consisting of oleanolic acid, medicagenic acid, sapogenol and hederagenin; said sapogenin having an ursane structure is selected from the group consisting of ursolic acid and asiatic acid.

11. The method of claim 4, wherein the relative weight ratio of said oxyacanthine component and of said saponin ranges between 10/1 and 1/10 by weight.

12. The method of claim 4, wherein the relative weight ratio of said oxyacanthine component and of said saponin is about 1/1.

13. A method of promoting hair growth, for delaying hair loss, for combating pruritus of an area of the body selected from the group consisting of hair and scalp, said method comprising the topical application to said area in an amount effective for achieving said desired effect, of an active ingredient consisting essentially of at least one oxyacanthine component selected from the group consisting of:

a) an oxyacanthine of formula (I) below:

[Chemical structure of formula (I)]

wherein R is hydrogen (oxyacanthine), a $C_1$–$C_{12}$ hydrocarbon chain, or a $C_2$–$C_{12}$ acyl radical, said hydrocarbon chain being selected from the group consisting of a saturated radical, an unsaturated radical, a linear radical, a branched radical, and a cyclic radical, said acyl radical being selected from the group consisting of a saturated radical, an unsaturated radical, a linear radical, a branched radical, and a cyclic radical, and b) an acid addition salt of said oxyacanthine of formula (I) defined under a), said oxyacanthine component being contained in hydrated lipidic lamellar phases or liposomes.

14. The method of claim 13, wherein said oxyacanthine component is in the form of a sulfuric acid addition salt.

15. A topical cosmetic or pharmaceutical composition consisting essentially of as active ingredient an oxyacanthine component selected from the group consisting of:

a) an oxyacanthine of formula (I) below:

[Chemical structure of formula (I)]

wherein R is hydrogen (oxyacanthine), a $C_1$–$C_{12}$ hydrocarbon chain, or a $C_2$–$C_{12}$ acyl radical, said hydrocarbon chain being selected from the group consisting of a saturated radical, an unsaturated radical, a linear radical, a branched radical, and a cyclic radical, said acyl radical being selected from the group consisting of a saturated radical, an unsaturated radical, a linear radical, a branched radical, and a cyclic radical, and b) an acid addition salt of said oxyacanthine of formula (I) defined under a);

said oxyacanthine being present in a concentration of at least 0.001% by weight with respect to the total weight of said composition, said composition containing a topically acceptable carrier for an application to the scalp or hair.

16. The composition of claim 15, wherein said oxyacanthine component is oxyacanthine.

17. The composition of claim 15, wherein R is selected from the group consisting of a methyl, hexyl, decyl, acetyl, propanoyl, butanoyl, hexanoyl and octanoyl radical.

18. The composition of claim 15, wherein said oxyacanthine of formula (I) is a sulfuric acid addition salt.

19. The composition of claim 15, wherein the concentration of said oxyacanthine component ranges between 0.001% and 5% by weight based on the total weight of said composition.

20. The composition of claim 15, wherein the concentration of said oxyacanthine component ranges between 0.01% and 2% by weight based on the total weight of said composition.

21. A cosmetic or pharmaceutical composition consisting essentially of as active ingredient an oxyacanthine component selected from the group consisting of:

a) an oxyacanthine of formula (I) below:

[Chemical structure of formula (I)]

wherein R is hydrogen (oxyacanthine), a $C_1$–$C_{12}$ hydrocarbon chain, or a $C_2$–$C_{12}$ acyl radical, said hydrocarbon chain being selected from the group consisting of a saturated radical, an unsaturated radical, a linear radical, a branched radical and a cyclic radical, said acyl radical being selected from the group consisting of a saturated radical, an unsaturated radical, a linear radical, a branched radical, and a cyclic radical, and b) an acid addition salt of said oxyacanthine of formula (I) defined under a), in combination with at least one saponin.

22. The composition of claim 21, wherein said saponin is selected from the group consisting of steroid saponins, triterpene saponins and mixtures thereof.

23. The composition of claim 22, wherein said steroid saponin is selected from the group consisting of saponins having diosgenin structures and saponins having sarsapogenin structures; wherein said triterpene saponin is selected from the group of saponins having oleanane structure and sapogenins having ursane structures.

24. The composition of claims 23, wherein said saponin having an oleanane structure is selected from the group consisting of oleanolic acid, medicagenic acid, sapogneol and hederagenin; said saponin having an ursane structure is selected from the group consisting of ursolic acid and asiatic acid.

25. The composition of claim 21, wherein the relative weight ratio of said oxyacanthine component and of said saponin ranges between 10/1 and 1/10 by weight.

26. The composition of claim 21, wherein the relative weight ratio of said oxyacanthine component and of said saponin is about 1/1.

27. The composition of claim 21, wherein said oxyacanthine component is contained in hydrated lipidic lamellar phases or liposomes.

28. The composition of claim 21, wherein said oxyacanthine component is in the form of a sulfuric acid addition salt.

29. The composition of claim 21, wherein the concentration of said oxyacanthine component ranges between 0.001% and 5% by weight based on the total weight of said composition.

30. The composition of claim 21, wherein the concentration of said oxyacanthine component ranges between 0.01% and 2% by weight based on the total weight of said composition.

31. A cosmetic or pharmaceutical composition consisting essentially of as active ingredient an oxyacanthine component selective from the group consisting of:

a) an oxyacanthine of formula (I) below:

[Structure of formula (I)]

wherein R is hydrogen (oxyacanthine), a $C_1$–$C_{12}$ hydrocarbon chain, or a $C_2$–$C_{12}$ acyl radical, said hydrocarbon chain being selected from the group consisting of a saturated radical, an unsaturated radical, a linear radical, a branched radical, and a cyclic radical, said acyl radical being selected from the group consisting of a saturated radical, an unsaturated radical, a linear radical, a branched radical, and a cyclic radical, and b) an acid addition salt of said oxyacanthine of formula (I) defined under a), and wherein said oxyacanthine component is contained in hydrated lipidic lamellar phases or liposomes.

32. The composition of claim 31, wherein the concentration of said oxyacanthine component ranges between 0.001% and 5% by weight based on the total weight of said composition.

33. The method of claim 4, wherein said oxyacanthine component is oxyacanthine.

34. The method of claim 4, wherein R is selected from the group consisting of a methyl, hexyl, decyl, acetyl, propanoyl, butanoyl, hexanoyl and octanoyl radical.

35. The method of claim 4, wherein said oxyacanthine component of formula (I) is sulfuric acid addition salt.

36. The method of claim 4, wherein the concentration of said oxyacanthine component ranges between 0.001% and 5% by weight based on total weight of said composition.

37. The method of claim 4, wherein the concentration of said oxyacanthine component ranges between 0.01% and 2% by weight based on the total weight of said composition.

38. The method of claim 4, wherein said saponin is selected from the group consisting of steroid saponins, triterpene saponins and mixtures thereof.

39. The method of claim 38, wherein said steroid saponin is selected from the group consisting of saponins having diosgenin structures and saponins having sarsapogenin structures; wherein said triterpene saponin is selected from the group of saponins having oleanane structure and sapogenins having ursane structures.

40. The method of claim 39, wherein said saponin having an oleanane structure is selected from the group consisting of oleanolic acid, medicagenic acid, sapogenol and hederagenin; said saponin having an ursane structure is selected from the group consisting of ursolic acid and asiatic acid.

41. The method of claim 4, wherein the relative weight ratio of said oxyacanthine component and of said saponin ranges between 10/1 and 1/10 by weight.

42. The method of claim 4, wherein the relative weight ratio of said oxyacanthine component and of said saponin is about 1/1.

43. The method of claim 4, wherein said oxyacanthine component is contained in hydrated lipidic lamellar phases or liposomes.

44. The method of claim 43, wherein said hydrated lipidic lamellar phases or liposomes further contain said saponin.

45. The method of claim 13, wherein said oxyacanthine component is oxyacanthine.

46. The method of claim 13, wherein R is selected from the group consisting of a methyl, hexyl, decyl, acetyl, propanoyl, butanoyl, hexanoyl and octanoyl radical.

47. The method of claim 13, wherein said oxyacanthine component of formula (I) is sulfuric acid addition salt.

48. The method of claim 13, wherein the concentration of said oxyacanthine component ranges between 0.001% and 5% by weight based on total weight of said composition.

49. The method of claim 13, wherein the concentration of said oxyacanthine component ranges between 0.01% and 2% by weight based on the total weight of said composition.

50. The method of claim 13, wherein said oxyacanthine component is in the form of a sulfuric acid addition salt.

51. A method of promoting hair growth, for delaying hair loss, and for combating pruritus associated with an area of the body selected from the group consisting of hair and scalp, said method comprising the topical application to said hair and scalp in an amount effective for achieving said desired effect, of an active ingredient consisting essentially of at least one oxyacanthine component selected from the group consisting of:

a) an oxyacanthine of formula (I) below:

[Structure of formula (I)]

wherein R is hydrogen (oxyacanthine), a $C_1$–$C_{12}$ hydrocarbon chain, or a $C_2$–$C_{12}$ acyl radical, said hydrocarbon chain being selected from the group consisting of a saturated radical, an unsaturated radical, a linear radical, a branched radical, and a cyclic radical, said acyl radical being selected from the group consisting of a saturated radical, an unsaturated radical, a linear radical, a branched radical, and a cyclic radical, and b) an acid addition salt of said oxyacanthine of formula (I) defined under a), said oxyacanthine being present in a concentration of at least 0.001% by weight with respect to the total weight of said composition;

said oxyacanthine component being contained in hydrated lipidic lamellar phases or liposomes; and said oxyacanthine component being combined with one saponin.

52. A topical cosmetic or pharmaceutical composition consisting essentially of as active ingredient an oxyacanthine component selected from the group consisting of:

a) an oxyacanthine of formula (I) below:

wherein R is hydrogen (oxyacanthine), a $C_1$–$C_{12}$ hydrocarbon chain, or a $C_2$–$C_{12}$ acyl radical, said hydrocarbon chain being selected from the group consisting of a saturated radical, an unsaturated radical, a linear radical, a branched radical, and a cyclic radical, said acyl radical being selected from the group consisting of a saturated radical, an unsaturated radical, a linear radical, a branched radical, and a cyclic radical, and b) an acid addition salt of said oxyacanthine of formula (I) defined under a);

said oxyacanthine being present in a concentration of at least 0.001% by weight with respect to the total weight of said composition, said oxyacanthine component being contained in hydrated lipidic lamellar phases or liposomes; and said oxyacanthine component being combined with one saponin, said composition containing a topically acceptable carrier for an application to the scalp or hair.

* * * * *